United States Patent [19]

Masilamani et al.

[11] 4,454,356

[45] Jun. 12, 1984

[54] PRODUCING METHYL ETHERS OF BRANCHED MONOOLEFINS

[75] Inventors: Divakaran Masilamani, Morristown; Andiappan K. S. Murthy, Lake Hiawatha, both of N.J.

[73] Assignee: Allied Corporation, Morris Township, Morris County, N.J.

[21] Appl. No.: 431,978

[22] Filed: Oct. 14, 1982

Related U.S. Application Data

[63] Continuation-in-part of Ser. No. 324,726, Nov. 25, 1981.

[51] Int. Cl.$^3$ .................... C07C 41/06; C07C 41/42; B01D 3/34
[52] U.S. Cl. ................................... 568/697; 203/38; 203/66; 203/70; 203/DIG. 6
[58] Field of Search ................. 568/697; 203/DIG. 6

[56] References Cited

U.S. PATENT DOCUMENTS

| | | | |
|---|---|---|---|
| 2,720,547 | 10/1955 | Wolff et al. | 260/614 |
| 4,232,177 | 11/1980 | Smith | 585/324 |
| 4,262,146 | 4/1981 | Childs | 568/697 |
| 4,292,219 | 9/1981 | Lyons et al. | 568/697 |

*Primary Examiner*—Natalie Trousof
*Assistant Examiner*—B. D. Gray
*Attorney, Agent, or Firm*—Alan M. Doernberg; Gerhard H. Fuchs; Kenneth E. Stroup

[57] ABSTRACT

Methanol is reacted with branched monoolefins such as isobutylene, or mixtures of hydrocarbons such as mixed C-4's from or in a refinery, in the presence of methanesulfonic acid. A column (10) operation is described wherein methanesulfonic acid (11) and methanol (12) are fed in countercurrent fashion to hydrocarbons (13). Crude product ether is removed as a liquid sidestream (25) above the feed of methanesulfonic acid (11), while hydrocarbons depleted of the reactive branched monoolefins (24) are removed overhead. The methanesulfonic acid suppresses the vapor pressure of methanol relative to product ether.

12 Claims, 3 Drawing Figures

PRODUCING METHYL ETHERS OF BRANCHED MONOOLEFINS

DESCRIPTION

This is a continuation-in-part of Ser. No. 324,726, filed Nov. 25, 1981.

BACKGROUND OF THE INVENTION

Methyl ethers of branched monoolefins such as methyl-t-butyl ether are known additives to gasoline which improve the octane rating of the mixture. Such methyl ethers are produced by reacting methanol with isobutylene, or the corresponding higher branched monoolefin, in the presence of an acidic catalyst. The reaction can proceed with mixed hydrocarbon streams containing the branched monoolefin, with most catalytic systems being generally economically limited to hydrocarbon streams containing at least about 50% of the desired branched monoolefin, typically in combination with other monoolefins, diolefins and alkanes.

Among the common catalysts for the reaction are zeolites, acidic ion exchange resins and acidic inorganic materials. The reaction is normally conducted either in a batch fashion or with co-current feed of methanol and hydrocarbon. Unfortunately, the most common source of branched monoolefins, such as isobutylene, is in refinery operations wherein the isobutylene is present as less than 50% of a hydrocarbon stream, and is frequently also present with butadiene. While linear monoolefins and alkanes (e.g., butane) are inert in the presence of methanol and such acidic catalysts, the presence of butadiene complicates the reaction with most conventional catalysts, producing by-products such as polybutadienes.

U.S. Pat. No. 4,218,569 to Chase et al. (1980) discloses a process of providing methyl-t-butyl ether (MTBE) suitable for gasoline-blending and C-4 hydrocarbons depleted of isobutylene suitable for alkylation. This patent indicates that simple distillation will not produce a C-4 overhead free of methanol in amounts objectionable for alkylation; and therefore the patent recommends passing the distillate through a solvent such as ethylene glycol to lower its methanol content to below 100 ppm. Such a method requires three steps—reaction, distillation and stripping—and the resultant complications and capital expense. If the methanol content (about 5 weight %) of the MTBE stream is to be lowered, a fourth step (methanol stripping of the MTBE) would be required. It would be desirable to produce depleted C-4 and MTBE streams both low in methanol directly.

U.S. Pat. No. 2,720,547 to Wolff et al. (1951) describes a process in which mixed butenes are fed adjacent to the bottom and a mixture of methanol and alkanesulfonic acids are fed adjacent the top of a reaction column operating at −50° C. to +50° C. An overhead stream containing unreacted butenes and a bottoms stream containing alkanesulfonic acid catalyst, methyl-t-butyl ether product and small amounts of methanol are both fed from the reaction column to a fractionating column operating at lower pressure, with excess methanol added to the bottoms stream. Four streams are removed from the fractionating column, one of which contains methyl-t-butyl ether and methanol as a azeotrope. Methanol is scrubbed from the methyl-t-butyl ether with water.

BRIEF DESCRIPTION OF THE INVENTION

The present invention includes an improvement in a process of producing a methyl ether by reacting methanol with a hydrocarbon stream comprising at least about 5 mole percent of at least one branched monoolefin of 4–6 carbons having a carbon bonded to exactly 3 other carbons in the presence of at least about 10 percent alkanesulfonic acid by mols of methanol; wherein said hydrocarbon stream is fed adjacent to the base of a reaction column, wherein said methanol and alkanesulfonic acid are fed intermediate the base and top of the reaction column, and wherein an overhead stream is removed containing hydrocarbons depleted in said branched monoolefin. In the improvement, the temperature of the reaction column at and below the alkanesulfonic acid feedpoint is sufficiently high for the operating pressure to cause the product methyl ether to migrate upward above said alkanesulfonic acid feedpoint in admixture with unreacted hydrocarbons, and wherein methanol is fed sufficiently below said alkanesulfonic acid feedpoint for methanol to be substantially absent from the reaction column above said alkanesulfonic acid feedpoint.

DETAILED DESCRIPTION OF THE INVENTION

The two reactants in the present process are methanol and a hydrocarbon stream. The catalyst is an alkanesulfonic acid or mixture of such acids, and is preferably methanesulfonic acid. Various high boiling neutral compounds such as esters, sulfones, sulfonate esters and sulfoxides may be used with the catalyst (alkanesulfonic acid) to lower the activity coefficient of methanol in the liquid phase. Two preferred such materials are methyl methanesulfonate and sulfolane, which appear to have the added advantages of reducing the corrosivity of the alkanesulfonic acids towards stainless steel and further decreasing the solubility of the product ether. Other additives, including other corrosion inhibitors or solubility modifers, may also be used with the catalyst.

The hydrocarbon stream must contain at least one branched monoolefin of 4–6 carbons such as 2-methylpropene (also called isobutylene). The branched monoolefins and their reaction products are as follows:

| Branched Monoolefin | Product Ether |
|---|---|
| 2-methylbutene-1 | 2-methyl,2-methoxybutane |
| 2-methylbutene-2 | 2-methyl,2-methoxybutane |
| 2-methylpentene-1 | 2-methyl,2-methoxypentane |
| 2-methylpentene-2 | 2-methyl,2-methoxypentane |
| 3-methylpentene-2 | 3-methyl,3-methoxypentane |
| 2-ethylbutene-1 | 3-methyl,3-methoxypentane |
| 2,3-dimethylbutene-2 | 2,3-dimethyl,2-methoxybutane |
| 2,3-dimethylbutene-1 | 2,3-dimethyl,2-methoxybutane |

Branched isomers having no branch point at a double bond (e.g., 4-methylpentene-1, 3-methylpentene-1, 4-methylpentene-2, 3-methylbutene-1) would not be expected to react to any appreciable extent, nor would conjugated diolefins.

The preferred branched monoolefin is isobutylene, with 2-methybutene-1 and 2-methylbutene-2 being next most preferred.

The branched monoolefin is frequently contained in hydrocarbon streams containing alkanes, other monolefins and, sometimes, diolefins. Thus, for example, isobutylene is produced in refinery operations in admixture with butane, 1-butene, 2-butenes, 1,3-butadiene, normal butane and isobutane. In some parts of the refinery, additional components, including methane, ethane, ethylene, propylene, and the like may also be present. In such so-called C-4 fractions, there may also be trace amounts of pentenes, pentanes, and pentadiene. In practicing the present invention, virtually all materials which are not branched monoolefins are essentially inert to the reaction conditions, and therefore may be present provided that the branched monoolefin is present in an amount of at least about 5 mol percent and preferably at least 10 mol percent. Thus, in a refinery wherein the gas fraction is first separated to remove lower hydrocarbons from the C-4 fraction, then debutanized to remove butane and thereafter distilled to remove butadiene, it is possible to practice the present invention on any of the various hydrocarbon streams: from the crude stream at the cracking unit wherein the hydrocarbons are generated to the purified stream at a point after butadiene removal, depending upon which of the streams first reaches an isobutylene concentration of at least about 5 percent. Furthermore, in refineries in which the light hydrocarbons generated from cracking exceed 5 percent isobutylene, but light hydrocarbons from reforming or from atmospheric distillation have lower contents of isobutylene, one may either practice the invention on the gas stream coming from the cracking unit, or may combine the three gas streams in conventional fashion, separate lower hydrocarbons such as methane, ethane, and ethylene, separate a liquid petroleum gas (propane) and thereafter practice the present invention so as to react isobutylene out of the gas stream and produce a gas stream containing 1-butene, 2-butenes, butadiene and butanes. It should be appreciated that, by removing isobutylene, distillation to purify the remaining components becomes easier because of the close boiling point between isobutylene and 1-butene.

In the present invention the hydrocarbon stream is passed in counter-current fashion to both the methanesulfonic acid and the methanol in a column arrangement. Because the etherification reaction reaches equilibrium under batch conditions of about 95 percent conversion at most conventional reaction pressures and temperatures, the use of counter-current reaction enables greater than 95 percent conversion of methanol at the point of hydrocarbon introduction and, concurrently, greater than 95 percent conversion of isobutylene at the point of methanol introduction. Futhermore, countercurrent flow faciliates the separation of the product (e.g., methyl-t-butyl ether) from methanol in spite of the relatively close boiling points. Heats of reaction can be used to effect the distillation.

It is an important feature of the present invention that the reaction temperatures at and below the feedpoint of alkanesulfonic acid (e.g., methanesulfonic acid) are sufficiently high to cause the product ether (e.g., methyl-t-butyl ether) to migrate upward in the column to above the feed point of alkanesulfonic acid. Under such conditions (typically 80°-120° C. at most convenient pressures) the downcoming catalyst will strip the vapor phase of methanol and prevent methanol (unless in excess) from migrating above the feed point of catalyst. At the same time, conditions upon which the product ether will decompose by the reverse reaction are avoided. This enables the product ether to be separated from hydrocarbons (a rather simple operation) rather than form the ether-methanol azeotrope. The feed of methanol is sufficiently below the feedpoint of catalyst to provide enough effective trays for the absorption of methanol by the liquid. The appropriate point or points of methanol feed can be determined as described below with no more than the routine amount of experimentation normally employed in designing an operating plant based upon the chosen hydrocarbon stream and operating pressure. It is expected that some of the methanol can be fed with the alkanesulfonic acid in addition to that fed below the feedpoint of alkanesulfonic acid. The alkanesulfonic acid/methanol stream can be fed as a liquid cooler than the liquid phase of adjacent plates of the column.

As stated above, representative temperatures for the reaction zone are about 80°-120° C., at least for the case of methanol reacting with isobutylene. A broad range generally suitable for practicing the reaction step of the present invention is 50°-130° C. A preferred range is about 70° to 90° C. if excess methanol is not present, but materials such as sulfolane are present. A preferred range is 80°-120° C. and especially 100°-120° C. excess methanol is present. As stated below, the preferred operating pressure range is 150-200 psig (1135-1480 kPa), with lower or higher pressures being suitable depending upon the pressure at which the other hydrocarbons not reacted by the present process are to be used downstream. A broad suitable range is 100-225 psig (790-1655 kPa).

Figure 1:
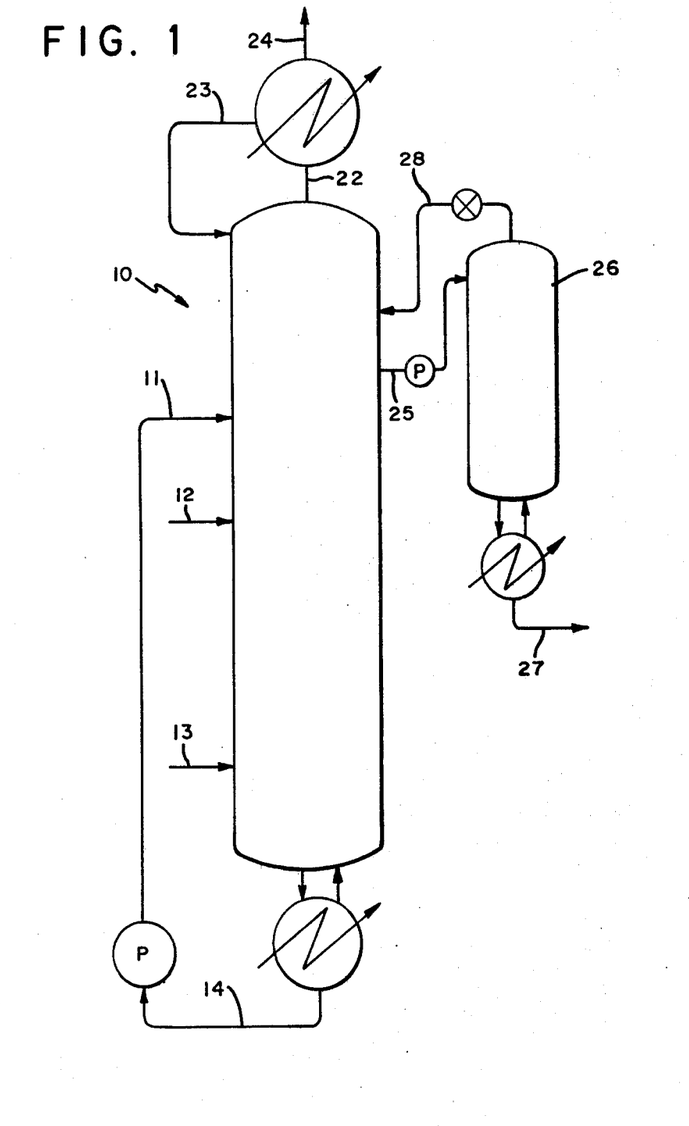
Figure 2:
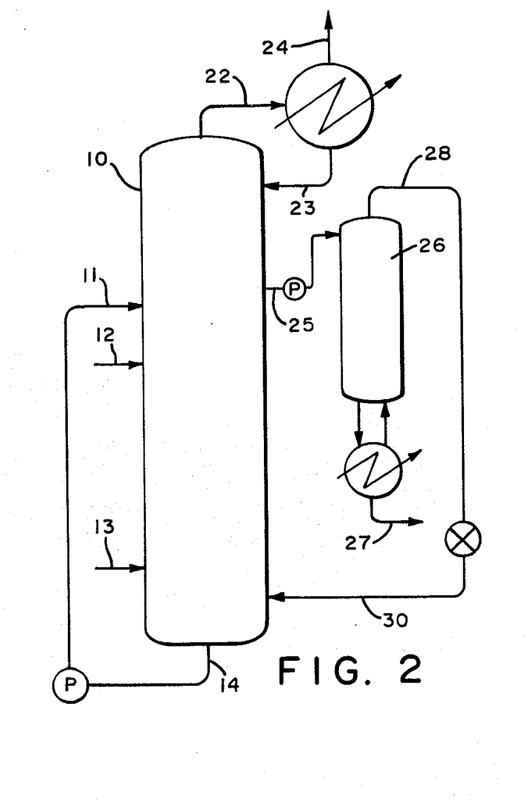
Figure 3:
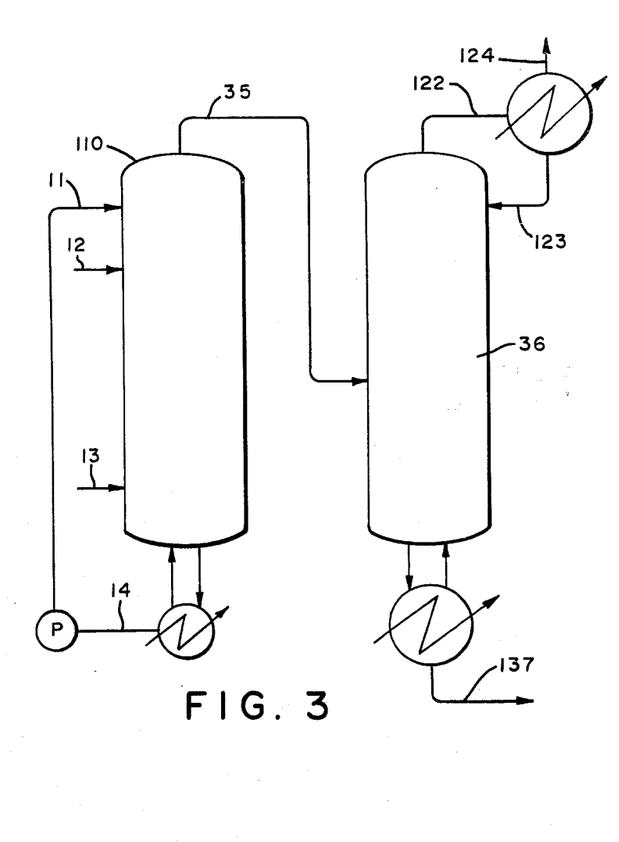

A preferred means of recovering the product ether is to remove a liquid sidestream containing product ether (e.g., methyl-t-butyl ether) and dissolved hydrocarbons and to distill this mixture (e.g., in device 26 in the figures) to produce a product ether with low hydrocarbon content. The unsaturated ingredients in these hydrocarbons (e.g., butadiene, 1-butene and 2-butenes) are undesirable impurities in the ether because of their tendency to polymerize over long periods of time and form sludge.

The overheads from this separate distillation will generally contain mostly hydrocarbons, and can be returned to the reaction column at any point such as above where the sidestream is withdrawn or adjacent the base of the reaction column.

DESCRIPTION OF THE PREFERRED EMBODIMENTS

One mode of practicing the process of the present invention is illustrated in FIG. 1 wherein element 10 is a distillation column, illustrated as multi-tray, but optionally of other configurations such as a packed column. A stream 11 containing methanesulfonic acid is fed to a tray near the middle of column 10. Below the feed of methanesulfonic acid stream 11, methanol is fed in stream 12 to the column. Near the base of the column, a third stream 13 containing a mixture of hydrocarbons, such as a C-4 stream containing 10-50 percent isobutylene, is fed to the column.

In the section of the column 10 at and below the feedpoint of stream 11, the methanesulfonic acid-catalyzed etherification reaction takes place, providing the ether which is methyl-t-butyl ether when the branched monoolefin is isobutylene. Because of the effect of methanesulfonic acid in suppressing the vapor pressure of methanol relative to the ether, both methanesulfonic acid and a small amount of unreacted methanol fractionate down the column and are removed as column bottoms in stream 14 which may be directly recycled to feedstream 11, or may be treated (e.g., by reboiling or by flashing and repressurization) to remove excess methanol so as to return essentially only methanesulfonic acid into stream 11. The methanol so removed may be recycled to the process, e.g., into stream 12.

The product ether and unreacted hydrocarbons (e.g., C-4's depleted of isobutylene) fractionate up the column above the feedpoint of stream 11. The vapor overhead containing almost exclusively hydrocarbons (stream 22) is cooled to condense any ether with mostly the hydrocarbons to provide the necessary reflux. The condensate is returned in stream 23 to the top of column 10.

At a point between the feedpoint of stream 11 and the top of column 10 (preferably close to the feedpoint of stream 11), a liquid sidestream 25 is removed which will contain ether and hydrocarbons. The amount of dissolved hydrocarbons in methyl-t-butyl ether is temperature-dependent such that distilling sidestream 25 in a sidestripper device 26, normally with only a few trays, produces a liquid product stream 27 very high in ether. The overheads 28 from device 26 will contain mainly hydrocarbons and some ether and can be returned at any convenient location to column 10, e.g., above sidestream 25 and below condensate return 23.

While the system of FIG. 1 may operate at any convenient superatmospheric pressure (e.g., the pressure at which further processing of hydrocarbon stream 24 will occur), the generally preferred operating pressues are about 100–225 psig (790–1655 kPa) because this range covers the pressures at which C-4 steams depleted of isobutylene are further processed. A typical operating pressure range is about 150–200 psig (1135–1480 kPa). Higher or lower pressures may be used, however, since various modifications may be made in the geometry to conform to pressure changes. Thus the spacing between the feedpoints of stream 11 and 12 should be sufficient to strip methanol out of the vapor and prevent such methanol from rising above the feedpoint of stream 11; otherwise, in the absence of methanesulfonic acid, methanol and methyl-t-butyl ether will separate (in a binary system) only gradually, if at all, unless the temperature and pressure are great enough to cause a significant difference in vapor pressures and boiling points. The hydrocarbons present (those not reacted in the reaction zone) form low boiling azeotropes with methanol, making it impossible to retain methanol in the column.

The operating pressure will also affect the required spacing between sidestream 25 and overhead stream 22 (to produce a vapor with low ether content). Pressure will also affect the spacing between other feedpoint locations and the required operating conditions to condense ether from stream 22 and to flash hydrocarbons from stream 25.

The heat of reaction is sufficient to support all of the distillation operations occurring in column 10, and especially to fractionate the ether product upward to sidestream 25, only when the amount of cold condensate returned in stream 23 is reasonably small. Often added heat may be required. Then stream 14 is passed through a reboiler to generate hot vapor (principally methanol) which is returned to the base of the column. The reboiler and the trays below stream 13 are used to strip isobutylene dissolved in the liquid phase and return it to the reaction zone. The heat balance may also be adjusted by feeding streams 11, 12 and/or 13 at temperatures below the reaction temperature (e.g., 15°–30° C.).

The use of methanesulfonic acid has the advantage that it permits hydrocarbon stream 13 to contain a relatively low (e.g., 10–30%) branched monoolefin content, further permits the column to operate at a high pressure and temperature without substantial polymer formation and, finally, is amenable to counter-current reaction with high conversion and easy separation of the product. In particular, methanesulfonic acid facilitates the separation of unreacted methanol from product ether and the unreacted hydrocarbons by suppressing the vapor pressure of methanol.

It has been discovered that the solubility of isobutylene in methanesulfonic acid/methanol mixtures is increased when some methyl-t-butyl ether is present in the liquid phase. Especially at lower pressures, the embodiment of FIG. 1 may have an insufficient rate of dissolution of isobutylene in the liquid near the feedpoint of stream 13, and this may act as the rate-limiting step.

The embodiment of FIG. 1 avoids two undesired reactions: polymerization of hydrocarbons and decomposition of ether. First, in the region of column 10 below the feed of methanol in stream 12, isobutylene is present predomininantly in the vapor phase and is normally present in the liquid phase at molar concentrations less than that of methanol. Under such conditions, even though the catalyst (methanesulfonic acid) is capable of catalyzing both etherification and polymerization, etherification proceeds much more rapidly and almost no polymers are formed.

Secondly, in the region of column 10 between the feedpoints of streams 11 and 12, and especially near the feedpoint of stream 11, methyl-t-butyl ether is present in far greater amounts than methanol or isobutylene. This is a consequence of the equilibrium for the reaction $$CH_3OH + CH_2 = C(CH_3)_2 \rightleftarrows CH_3\text{-}O\text{-}C(CH_3)_3$$

that normally results in the ether representing 95 mol % or more of the total mixture of ether and alcohol at temperatures of 80°–120° C. and low isobutylene levels, and with the ether being at molar levels greater than that of the catalyst.

The above equilibrium reaction would be shifted to the left (resulting in net product decomposition) by a combination of (a) high concentration of product ether in the liquid phase with a catalyst, (b) low methanol in the liquid phase and (c) high temperature. These conditions are avoided throughout column 10 in FIG. 1. At and below the feed of stream 11, these conditions are avoided because of a high concentration of methanol relative to isobutylene in the liquid phase and by a low concentration of ether in the liquid phase (even though the ether is of high concentration in the vapor phase). Near the feed of stream 13, the ether (in both phases) is low and isobutylene is in high concentration. The liquid and vapor at levels even slightly (i.e., one or two trays) above the feedpoint of stream 11 will have essentially no catalyst and almost no methanol; and in the absence of catalyst, the product ether will not decompose.

It has been found that conditions of low methanol in both phases above the feedpoint of stream 11 can be maintained even if methanol is recycled in stream 14. So long as make-up methanol in stream 12 is limited to the amount actually consumed by the reaction, steady-state operations can occur with stream 11 containing some methanol.

The temperature in the rectification section below the return of stream 23 and above the feed of stream 11 will generally be lower than that of the reaction zone including the feedpoint of stream 11 and below. Depending upon operating pressure, this zone will be in the general range of 30°–100° C., normally with a 15°–30° C. gradient between the returns of streams 23 and 28.

The operating conditions of device 26 may be similar to that of the rectification zone, but will generally be at slightly higher pressure and moderately higher temperatures (e.g., 5°–10° C. higher). Such pressures can be maintained by pumping liquid stream 25 and passing vapor stream 28 through a let-down valve before return to column 10.

FIG. 2 illustrates a second embodiment of the invention in which are fed to reaction column 10 methanesulfonic acid with some hydrocarbons, ether and methanol in stream 11, methanol in stream 12 and mixed C-4 hydrocarbons (e.g., 10–50% isobutylene) in stream 13. The bottoms in stream 14 are recycled to stream 11, here without a reboiler. A liquid sidestream 25 containing product methyl-t-butyl ether and some hydrocarbons is removed above the catalyst feedpoint of stream 11 and separated in sidestripper device 26 into a bottoms stream 27 containing product ether with only traces of hydrocarbons and an overheads 28. In all respects except the failure to reboil the bottoms stream 14 and slight adjustments to the location of various feeds, the aspects of the embodiment of FIG. 2 described thus far are identical to similarly numbered features of the embodiment of FIG. 1. In the embodiment of FIG. 2, however, the overhead stream 28 from device 26 is fed in stream 30 back to the lower section of column 10 below the feed of methanol in stream 12. Stream 30 should be fed below stream 13 and preferably below the bottom tray of the column. Because stream 30 contains mostly unreacted hydrocarbons, but also significant amounts (e.g., 10–45 mol %) of methyl-t-butyl ether, it will have three effects on the composition of materials in column 10, and especially the portion thereof below the feed of stream 11. First, the proportion of isobutylene as a fraction of total hydrocarbons will be lessened and thus the reaction rate near the feed of stream 13 may be lessened. This effect is normally not deleterious unless the isobutylene content of stream 13 is particularly low (e.g., 5 mol %) and may assist in temperature distribution. The second effect is to significantly increase the methyl-t-butyl ether level adjacent the feedpoint of stream 13 and below. Because isobutylene is more soluble when ether is present, this second effect alters the partitioning of isobutylene between the gaseous and liquid phases in such a way as to increase the relative amount present in the liquid layer; this generally results in much higher levels of isobutylene being available for reaction, and thus increases the reaction rate, even though the total proportion of isobutylene is less, because of the first effect.

The third effect is to make the latent heat in streams 28 and 30 (from the reboiler of device 26) available to the lower section of reaction column 10 rather than the upper section. The advantage of this third effect is that no reboiler in stream 14 is normally required since the combination of latent heat in stream 28 and heat of reaction should normally suffice to strip the product ether and dissolved isobutylene upward. The disadvantage is that control of distillation operations may be somewhat less direct in that more heat must be added to the reboiler of device 26 in order to indirectly increase the latent heat supplied to the base of column 10. It is contemplated to modify the embodiment of FIG. 2 to have a reboiler in stream 14 for occasional use for control purposes. It is also contemplated to feed a portion of overhead stream 28 of device 26 in FIG. 1 back to the base of column 10 (in the manner of stream 30 of FIG. 2) to reduce the load on the reboiler.

However, if stream 30 contains methyl-t-butyl ether, there will be an increase in the methyl-t-butyl ether content of stream 14. Methyl-t-butyl ether in stream 14 may become subject to decomposition, especially if the methanol content of stream 14 is low and the residence time in stream 14 at high temperatures is long. For example, if stream 14 is subjected to heat treatment for removal of impurities, this residence time increases. On the other hand, if stream 14 is cooled before reintroduction, or has a short residence time, the deleterious effects will be minimized.

FIG. 3 illustrates a third embodiment of the process of the present invention. Alkanesulfonic acid in stream 11, methanol in stream 12 and mixed C-4 hydrocarbons in stream 13 are fed to points adjacent the top, in the middle and adjacent the bottom, respectively, of column 110. The bottoms of column 110 are withdrawn in stream 14 with a reboiler and recirculated to stream 11. In most respects, column 110 operates in a manner similar to the bottom portion of column 10 in FIGS. 1 and 2 to produce alkanesulfonic acid with some methanol, ether and hydrocarbons in stream 14 and a mixture of ether and unreacted hydrocarbons as the vapor phase near the feedpoint of stream 11. One or a few trays may be provided above the feedpoint of stream 11 to remove any entrained liquid (or a demister or other device may be used). The vapor overheads from column 110 are fed in stream 35 to a fractional distillation column 36. Column 36 is operated with both a reboiler and reflux to produce an overheads 122 rich in unreacted hydrocarbons with only small amounts of ether. By condensing the overheads, some of the hydrocarbons and essentially all of the ether is returned to column 36 in reflux stream 123, with the remaining vapor product 124 being hydrocarbons depleted of isobutylene and containing only trace amounts of ether and methanol. The bottoms product in stream 137 contains methyl-t-butyl ether of high purity.

It is contemplated that the embodiment of FIG. 3 may be modified in various respects, as by using slight reflux on column 110, by splitting column 36 into a hydrocarbon recovery column and a product ether recovery column or by returning one or more sidestreams from column 36 to column 110 in the manner of stream 30 of FIG. 2. The embodiment of FIG. 3 has the advantage over those of FIGS. 1 and 2 of isolating the reaction in column 110 apart from both purification operations so that the reboiler on stream 14 affects mainly the reaction zone only. The use of a large vapor stream 35 may have disadvantages, however, and column 36 may be difficult to operate in a manner that ensures both low ether content in stream 122 and low hydrocarbon content in stream 137.

EXAMPLE 1

Methanesulfonic Acid Catalyzed Addition of Methanol to Isobutylene

Methanol (6.4 g; 0.2 mol.) and methanesulfonic acid (3.6 g; 0.0375 mol.) were condensed into a 100 ml Fisher Bottle. Isobutylene (10.4 g; 0.185 mol) was condensed into the bottle at −20°. The bottle was closed and heated in a bath maintained at 70°. The pressure rose to 85 psig (687 kPa absolute) in 5 min. and then dropped to a constant value of 34 psig (336 kPa absolute) at 15 min.

The bottle was cooled to room temperature. The pressure dropped to 0 psig (101 kPa absolute) indicating that the isobutylene had reacted completely. The colorless liquid product was analyzed by NMR spectrocopy. A complete conversion of isobutylene to methyl-t-butyl ether (MTBE) was evident. No products other than MTBE, excess methanol and methanesulfonic acid (catalyst) were observed.

The crude product on distillation (bp 50° C.) yielded 13.1 g of colorless liquid. NMR of this liquid showed MTBE (78.6%), methanol (10.7%) and isobutylene (10.7%). It is obvious that methanol and isobutylene were formed during distillation by the acid catalyzed cracking of MTBE. The residue (5.5 g) showed methanesulfonic acid along with trace amounts of methanol.

EXAMPLE 2

Methanesulfonic Acid Catalyzed Addition of Methanol to Isobutylene at 120°

A mixture of methanol (3 g; 0.093 mol.), methanesulfonic acid (1.7 g; 0.0176 mol.) and isobutylene (4.8 g; 0.085 mol.) was heated at 120° for 15 min. in a stainless steel bomb. After cooling, the bomb was opened and the contents analyzed by NMR spectroscopy. The product mixture was made up of MTBE, excess methanol and methanesulfonic acid along with small amounts (less than 5%) of the dimers and trimers of isobutylene.

The above experiment was repeated with 3.75 g. (0.0176 acid equivalent) of Amberlyst 15 as a catalyst. The products were identical. However, the trimers and dimers of isobutylene were present to an extent of 10%.

EXAMPLE 3

MTBE as a Solvent in the Methanesulfonic Acid Catalyzed Addition of Methanol to Isobutylene Methanol (8 g.; 0.25 mol.) and methanesulfonic acid (3.5 g; 0.036 mol.) were taken in a 100 ml Fisher bottle. After flushing the bottle five times with isobutylene, the contents were stirred at 55° under a constant pressure of isobutylene at 26 psig (281 kPa absolute) Samples were withdrawn at 15, 30, 45, 60, 90 and 120 min. and quenched in $D_2O$. The NMR spectrum was recorded for each sample. From these spectra, the MTBE formed was calculated to be respectively 20.1%, 30.78%, 47.69%, 62.17%, 83.66% and 95.90%.

The data clearly show that the rate of MTBE formation increases with time. Isobutylene is more soluble in MTBE than methanol. As MTBE is formed in the course of the reaction, the concentration of isobutylene dissolved in the liquid phase increases and consequently the rate of MTBE formation increases.

By dissolving methanol (4 g; 0.125 mol.) and methanesulfonic acid (3.5 g; 0.036 mol.) in a large excess of MTBE (44 g; 0.5 mol.) and pressurizing this solution with isobutylene at a constant pressure at 28 psig (294 kPa absolute) at 45°, the solubility of isobutylene was maintained constant in course of the reaction. Under these conditions, a pseudo-first order rate constant of $5.57 \pm 0.09 \times 10^{-3}$ min$^{-1}$ (up to four half lives) was observed for the consumption of methanol.

EXAMPLE 4

Selectivity Test for Methanesulfonic Acid Catalysis in MTBE Formation

Methanol (3.45 g; 0.108 mol.) and methanesulfonic acid (1.92 g; 0.02 mol.) were taken in a 100 ml Fisher Bottle. 1-Butene (5.6 g; 0.1 mol.) was condensed into the bottle at $-20°$. The bottle was closed and heated at 70° for 3 hours. The pressure remained constant at 100 psig (791 kPa absolute) thereby indicating that 1-butene did not react with methanol. The bottle was cooled to room temperature and the gas was released slowly and condensed (using a Dewar condenser cooled by dry-ice and acetone mixture) into a flask containing $CDCl_3$. The NMR spectrum of the $CDCl_3$ solution of the condensed gas showed only unreacted 1-butene. There was no indication of isomerization or polymerization of 1-butene. The residue in the bottle was entirely made up of methanol and methanesulfonic acid. There was no indication of ether products.

The above experiment was repeated individually with 0.1 mol of 1,3-butadiene, cis and trans-2-butenes. None of these olefins reacted with methanol even after 3 hours of heating at 70°. Thus, methanesulfonic acid exclusively catalyzes the addition of methanol to isobutylene and not to any of the other four carbon unsaturates.

EXAMPLE 5

Methanesulfonic Acid Catalyzed Addition of Methanol to Isobutylene in the Presence of Other Four-Carbon Unsaturates Methanol (6.4 g; 0.2 mol.) and methanesulfonic acid (3.6 g; 0.0375 mol.) were taken in a 100 ml Fisher bottle. A mixture (11.2 g.) of four-carbon unsaturates (containing 11.1% 1-butene, 20.8% cis-2-butene, 24.2% butadiene, 18.8% isobutane and 25% isobutylene) was condensed into the bottle and heated at 70° for 30 min. The pressure rose to a maximum of 100 psig (791 kPa absolute) at 15 min. and dropped to 95 psig (756 kPa absolute) at 30 min. The heating was stopped and the bottle was cooled to room temperature. Two liquid phases were observed. Analysis of the gas phase and the top liquid layer showed only hydrocarbons. Isobutylene was observed to an extent of less than 2% in these phases. The lower liquid layer showed only MTBE, excess methanol, methanesulfonic acid and trace amounts of dissolved olefins. The ratio of methanol to MTBE was 2.95. The expected ratio was 3.0.

The above experiment was repeated with 2.4 g (0.075 mol.) of methanol and 1.35 g (0.014 mol.) of methanesulfonic acid with 16.8 g of the above carbon-four unsaturates (in which isobutylene is present in 0.075 mol quantity). The reaction was carried out at 70° C. for 30 min. Analysis of the gaseous and liquid hydrocarbon phases showed less than 2% of isobutylene. The lower liquid layer showed only MTBE and methanesulfonic acid along with trace amounts of methanol and dissolved olefins.

EXAMPLE 6

Recycling Metnanesulfonic Acid Catalyst

Methanol (5.5 g; 0.172 mol.) and methanesulfonic acid (2.4 g; 0.025 mol.) were taken in a Fisher Bottle (100 ml). Isobutylene (8.3 g; 0.148 mol.) was condensed into the bottle at $-20°$. The bottle was closed and heated at 70° for 20 min. The pressure rose to 90 psig (722 kPa absolute) in 5 min and dropped to 34 psig (366 kPa) and remained constant after 15 min. The bottle was cooled to room temperature and the product distilled to yield 11.2 g (bp 44°-53°) of colorless liquid which was made up of 84% of MTBE and 16% of methanol. Only trace amounts of isobutylene were observed.

The residue (3.9 g) was made up of MTBE, methanol and methanesulfonic acid in the molar ratio of 1:3:3. The residue was reused as the catalyst in a second experiment reacting 4.8 g (0.15 mol.) of methanol and 8.3 g (0.148 mol.) of isobutylene under identical conditions to those described above. The distillate in the second experiment was made up of 92% MTBE and 8% methanol.

The residue was reused a third time as a catalyst without any loss in the catalytic activity.

EXAMPLE 7

Methanesulfonic Acid Catalyzed Addition of Methanol to 2-Methyl-2-butene

Methanol (3.5 g; 0.109 mol.), methanesulfonic acid (2.3 g; 0.024 mol.) and 2-methyl-2-butene (7 g; 0.1 mol.) were stirred at 70° in a 100 ml. Fisher bottle for 1 hour. Two liquid layers persisted during the course of the reaction. The pressure initially rose to 24 psig (267 kPa absolute) at 10 min. but stabilized at 20 psig (239 kPa absolute) after 14 min.

After cooling to room temerature, the two layers were separated. The upper layer was made up of t-amylmethylether (TAME) or 2-methoxy-2-methylbutane.

EXAMPLE 8

The example indicates the influence of added methanesulfonic acid and methyl methanesulfonate on the composition of methanol, MTBE and 1,3-butadiene in the vapor phase. The butadiene was used to simulate isobutylene, which would be reactive under these conditions.

An equimolar mixture of methanol, MTBE and 1,3-butadiene was taken in a Fisher bottle. The bottle was cooled in liquid nitrogen and evacuated with a pump at 0.1 mm (13 Pa). The bottle was warmed to room temperature, re-cooled and re-evacuated at 0.1 mm (13 Pa). The freeze-thaw techniques was repeated two more times.

The bottle was finally heated at 45° or 65° in a thermostated bath for 30 minutes. A sample of the vapor phase was analyzed both by gas chromatography and NMR spectrocopy, giving the values shown in columns A below.

The same experiment was repeated with an equimolar amount of methanesulfonic acid (columns B below) and an equimolar mixture of methanesulfonic acid and its methylester (columns C below). The results are tabulated below.

|  | A | B | C |
|---|---|---|---|
| At 45° C. (Mol % In Vapor Phase) | | | |
| Methanol | 7.2 | 6.9 | 3.4 |
| MTBE | 7.2 | 18.1 | 7.5 |
| 1,3-Butadiene | 85.6 | 75.0 | 89.0 |
| At 65° C. (Mol % In Vapor Phase) | | | |
| Methanol | 11.5 | 8.4 | 7.8 |
| MTBE | 9.1 | 13.1 | 17.2 |
| 1,3-Butadiene | 79.4 | 78.5 | 75.0 |

EXAMPLE 9

Stability of MTBE in Methanesulfonic Acid

A mixture of MTBE and methanesulfonic acid in a 1:1 molar ratio, when stirred at room temperature, decomposed and formed two layers after 45 minutes. No gas evolution was observed. The top layer was entirely made up of the dimers and trimers of isobutylene and MTBE. The lower layer contained methanesulfonic acid and methanol in the ratio of 2:1. Small amounts of MTBE were also present in this layer. About one-third of the MTBE has been decomposed in 45 minutes.

A mixture of MTBE and methanesulfonic acid in a 3:1 molar ratio was stable at room temperature for 6 hours. After 6 hours, trace amounts of methanol was observed. After standing overnight, the reaction mixture was analyzed. The composition was identical to the one analyzed after 6 hours.

A mixture of MTBE, methanesulfonic acid and methanol in a 1:1:1 molar ratio was also stable indefinitely at room temperature.

MTBE is stable in the presence of methanesulfonic acid at higher temperatures. Thus a mixture of MTBE and methanesulfonic acid in a 1:1 molar ratio is only decomposed to an extent of 15% at 45° C. in 45 minutes. At higher ratios of MTBE, the stability is greater at higher temperatures as well.

EXAMPLES 10-13

Feasibility Studies with a Small-Scale Reactor

A small reactor made of stainless steel pipe (33¼" long, ⅝" in diameter and ⅛" thick) (106 cm, 1.58 cm, 0.317 cm) was filled to an extent of 78%, by volume, with glass helical packing (helix dimensions of 0.64 cm by 0.32 cm). The reactor was heated by means of electrical heating tapes. A methanesulfonic acid (MSA)-sulfolane mixture was preheated to the appropriate temperature and fed at the top of the reactor. Methanol was preheated and fed at a point near the middle of the reactor. Isobutylene and nitrogen (1:3 molar ratio) were fed at constant rates at the bottom of the reactor. The pressure of the reactor was controlled by a back-pressure valve and maintained at 100 psig (790 kPa). Gas samples from the top of the reactor and liquid samples collected at the bottom were analyzed by gas chromatagraphy and NMR spectroscopy. Gas flow rates were measured using a volumetric gas flow-meter. The temperature of the reactor was monitored at three locations—the top, the bottom and the middle. After the system had attained a steady state, samples were withdrawn and analyzed. The following Table 1 summarizes the results obtained for four different steady state conditions.

TABLE 1

| Example | Temp. of Reactor °C. | | | Polymers formed g/mol/min | Mol % of methanol in gas phase | MTBE formed g/mol/min |
|---|---|---|---|---|---|---|
| | Bottom | Middle | Top | | | |
| 10 | 81 | 75 | 53 | None | 0 | 0.0045 |
| 11 | 88 | 82 | 58 | 0.0034 | 0.1 | 0.0087 |
| 12 | 113 | 76 | 54 | 0.0020 | 1.6 | 0.0113 |
| 13 | 125 | 77 | 51 | 0.0028 | 5.0 | 0.0058 |

Note:
Isobutylene feed rate = 0.0338 g-mol/min
Methanol feed rate = 0.02267 g-mol/min
Ratio of methanol/catalyst = 1.79
Catalyst: a 1:1 molar ratio of methanesulfonic acid and sulfolane From the table it is clear that MTBE can be formed unaccompanied by polymer formation. Further, methanol can be prevented from forming an azeotrope in the gas-phase.

EXAMPLE 14

Inhibition of MTBE decomposition and azeotrope-formation between methanol and MTBE by using MSA-sulfolane-methanol complex A mixture made up of methanesulfonic acid (1.92 g; 0.02 mol), methanol (0.64 g; 0.02 mol), sulfolane (2.4 g; 0.02 mol) and MTBE (17.6 g; 0.2 mol) was distilled over a water bath at 80° C. at atmospheric pressure. The distillate was collected in a flask cooled at −10° C. The distillate weighed 16.4 g (93.1% yield) and was made up of MTBE and trace amounts of isobutylene. The residue (5.9 g) contained all the charged methanesulfonic acid, methanol and sulfolane and 1.0 g of MTBE. In this experiment about 1% of MTBE is not accounted for and it is assumed to have undergone decomposition during distillation.

The residue was further heated at 120° C. for an hour without losing the methanol and MTBE. The residue so heated is still efficient as a catalyst for MTBE formation.

The addition of sulfolane to methanesulfonic acid not only prevents azeotrope formation between methanol and MTBE, it inhibits the decomposition of MTBE as well.

EXAMPLE 15

The following represents a computer simulation of a large-scale embodiment of the process of the present invention based on the mode illustrated in FIG. 2. The stream numbers refer to FIG. 2. In this example, column 21 would include a condenser (to provide reflux) and is operated as a distillation column with sufficient number of trays to provide the desired purification of both hydrocarbon in stream 28 and ether in stream 27. For simplicity, butadiene is assumed to be the sole non-reactive olefin; however, other non-reactive four-carbon olefins will have only very minor effects because of similar vapor pressures.

A gas stream (13) at 100° C. containing 20% isobutylene and 80% butadiene (by volume) is fed at a rate of 100 g mol/sec at the fourth tray (counting from the bottom) of a 40 tray column maintained at 1135 kPa. Methanol at 100° C. is fed (stream 12) at the sixth tray at a design rate of 20 g mol/sec. Since feed rates of the various streams are subject to fluctuation, actual methanol feed is adjusted by feedback control so that the methanol feed is stoichiometric to isobutylene conversion in the reactor. Methanesulfonic acid circulation is maintained at a rate of 20 g mol/sec and the feedpoint for the acid is the 16th tray. At steady state, the acid recycle stream (11 and 14) will contain approximately 2 mole percent methanol, 4% MTBE and 30% butadiene with the balance being methanesulfonic acid.

A sidestream is withdrawn from the 18th tray at a rate of 60 g mol/sec. The sidestream will consist of 33% MTBE and 67% butadiene and traces of methanol. This stream is separated into a liquid stream of MTBE and a vapor stream of butadiene. Because of the high relative volatilities, few trays are required. The vapor stream is recycled to the bottom of the reactor column 10.

At the top of the reactor column 10, a partial condenser is used to provide an external reflux ratio of 1.5. At the column operating pressure of 1135 kPa, the condenser will operate at 75° C. The temperature of the side stream will be 87° C. Below the acid feed stream 11, temperatures will range from 100° C. to 117° C. This system is summarized in Table 2.

Based upon this simplified case and the teachings in this Specification, other modes of practicing the invention for a particular hydrocarbon feed stream, desired pressure and other conditions can be determined. Modifications are contemplated in this system including returning some ether with stream 30; feeding various streams at those temperatures and states at which they are available (i.e. not at 100° C.); cooling recycle stream 11; addition of some fresh methanol to stream 11; splitting any one or more of streams 11, 12, 13 and 30. For any particular system, parameters such as number of trays, reflux ratio and exact feedpoints can be optimized in the normal fashion. The above example has not been so optimized, but instead is based upon parameters selected arbitrarily in advance based upon preliminary evaluations comparing this process with existing technologies. Actual operating conditions may include, for example, a reflux ratio less than 1.5.

TABLE 2

| Tray | Stream | Total g-mol/ second | MSA | IB | BD | MeOH | MTBE | Temp °C. |
|---|---|---|---|---|---|---|---|---|
| 16 | 11 | ** | 64 | — | 30 | 2 | 4 | 100 |
| 6 | 12 | 20* | — | — | — | 100 | — | 100 |
| 4 | 13 | 100 | — | 20 | 80 | — | — | 100 |
| 0 | 14 | ** | 64 | — | 30 | 2 | 4 | 101 |
| 40 | 24 | 80 | — | trace | 100 | trace | trace | 75 |
| 18 | 25 | 60 | — | trace | 67 | trace | 33 | 87 |
| 1 | 30 | 40 | — | — | 100 | — | trace | 100*** |

*subject to adjustment by feedback control
**the initial MSA in 20 g mol/sec - the steady state composition is as indicated with 20 g/sec MSA
***for calculation purposes - would be fed at about 80° C. if stream 28 was produced at that temperature
MSA = methanesulfonic acid
IB = isobutylene
BD = butadiene
MeOH = methanol
MTBE = methyl-t-butyl ether

What is claimed is:

1. In a process of producing a methyl ether by reacting methanol with a hydrocarbon stream comprising at least about 5 mole percent of at least one branched monoolefin of 4-6 carbons having a carbon bonded to exactly 3 other carbons in the presence of at least about 10 percent alkanesulfonic acid by mols of methanol; wherein said hydrocarbon stream is fed adjacent to the base of a reaction column, wherein said methanol and methanesulfonic acid are fed intermediate the base and top of the reaction column, and wherein an overhead stream is removed containing hydrocarbons depleted in said branched monoolefin; the improvement wherein the temperature of the reaction column at and below the alkanesulfonic acid feedpoint is sufficiently high for the operating pressure to cause the product methyl ether to migrate upward above said alkanesulfonic acid feedpoint in admixture with unreacted hydrocarbons, and wherein methanol is fed sufficiently below said alkanesulfonic acid feedpoint for methanol to be substantially removed from the reaction column above said alkanesulfonic acid feedpoint.

2. The process of claim 1 wherein said alkanesulfonic acid is methanesulfonic acid.

3. The process of claim 2 wherein said branched monoolefin is isobutylene and said methyl ether is methyl-t-butyl ether.

4. The process of claim 3 wherein the temperature at and below the methanesulfonic acid feedpoint is between about 80° and about 120° C. and the pressure of said reaction column is between about 790 and about 1655 kPa.

5. The process of claim 4 wherein said pressure is between about 1135 and about 1480 kPa.

6. The process of claim 4 wherein the temperature at and below the methanesulfonic acid feedpoint is between about 100° and about 120° C. and excess methanol is present beyond that reacted with isobutylene.

7. The process of claim 4 wherein the temperature at and below the methanesulfonic acid is between about 70° and about 90° C. and said reaction is conducted in the presence of sulfolane mixed with methanesulfonic acid.

8. The process of claim 3 wherein the mixture of methyl-t-butyl ether with hydrocarbons above the methanesulfonic acid feedpoint is separated by distillation to produce a vapor comprising hydrocarbons with no more than minor impurities and a liquid comprising methyl-t-butyl ether with no more than minor impurities.

9. The process of claim 8 wherein methyl-t-butyl ether is stripped from the vapor phase in the reaction column above the feedpoint of methanesulfonic acid, wherein a liquid side-stream is removed from the reaction column above and adjacent the methanesulfonic acid feedpoint, wherein the liquid side-stream is distilled to produce a liquid comprising methyl-t-butyl ether and a vapor mixture comprising methyl-t-butyl ether and hydrocarbons, and wherein the vapor mixture is returned to the reaction column.

10. The process of claim 9 wherein the vapor mixture is returned to the reaction column above the point where the liquid side-stream is removed.

11. The process of claim 9 wherein the vapor mixture is returned to the reaction column adjacent the base of the reaction column.

12. The process of claim 3 wherein said hydrocarbon stream comprises between about 10 and 50 percent isobutylene.

* * * * *

UNITED STATES PATENT AND TRADEMARK OFFICE
CERTIFICATE OF CORRECTION

PATENT NO. : 4,454,356
DATED : June 12, 1984
INVENTOR(S) : D. Masilamani and A.K.S. Murthy It is certified that error appears in the above—identified patent and that said Letters Patent are hereby corrected as shown below:

Col. 15, line 9, "removed" should read --absent--

Signed and Sealed this

Twenty-third Day of October 1984

[SEAL]

Attest:

GERALD J. MOSSINGHOFF

Attesting Officer     Commissioner of Patents and Trademarks